United States Patent [19]
Gelbfish

[11] Patent Number: 5,730,717
[45] Date of Patent: Mar. 24, 1998

[54] METHOD AND ASSOCIATED DEVICE FOR REMOVING MATERIAL FROM BODY

[76] Inventor: Gary A. Gelbfish, 2502 Ave. I, Brooklyn, N.Y. 11210

[21] Appl. No.: 573,323

[22] Filed: Dec. 15, 1995

Related U.S. Application Data

[63] Continuation-in-part of Ser. No. 358,209, Dec. 16, 1994, Pat. No. 5,520,635.

[51] Int. Cl.$^6$ ................................................. A61B 17/20
[52] U.S. Cl. ................................. 604/22; 604/28; 604/93; 604/158; 604/280; 606/171; 128/753; 128/772
[58] Field of Search ............................... 604/21–22, 28, 604/30, 49, 51, 93, 158, 164, 170, 246, 256, 264, 268, 280; 606/107, 110, 115, 166, 167, 170–172; 128/751–755, 4, 772

[56] References Cited

U.S. PATENT DOCUMENTS

| | | |
|---|---|---|
| 3,693,613 | 9/1972 | Kelman . |
| 3,844,272 | 10/1974 | Banko . |
| 3,882,872 | 5/1975 | Douvas et al. . |
| 3,912,168 | 10/1975 | Mullins et al. . |
| 3,945,375 | 3/1976 | Banko . |
| 3,993,054 | 11/1976 | Newman . |
| 4,167,943 | 9/1979 | Banko . |
| 4,167,944 | 9/1979 | Banko . |
| 4,203,444 | 5/1980 | Bonnell et al. . |
| 4,428,748 | 1/1984 | Peyman et al. . |
| 4,493,694 | 1/1985 | Wuchinich . |
| 4,516,398 | 5/1985 | Wuchinich . |
| 4,555,645 | 11/1985 | Atkinson . |
| 4,589,412 | 5/1986 | Kensey . |
| 4,604,089 | 8/1986 | Santangelo et al. . |
| 4,631,052 | 12/1986 | Kensey . |
| 4,634,420 | 1/1987 | Spinosa et al. . |
| 4,646,736 | 3/1987 | Auth . |
| 4,669,469 | 6/1987 | Gifford, III et al. . |
| 4,670,006 | 6/1987 | Sinnett et al. . |

(List continued on next page.)

FOREIGN PATENT DOCUMENTS

| | | |
|---|---|---|
| 1069398 | 5/1967 | United Kingdom . |
| 2018601 | 10/1978 | United Kingdom . |

OTHER PUBLICATIONS

Drasler et al., "Rheolytic Catheter for Percutaneous Removal of Thrombus," *Radiology*, 1992; 182:263–267.

"Introducing the AngioJet" brochure, 1993, Possis Medical Inc., Minneapolis, MN.

*Primary Examiner*—Vincent Millin
*Assistant Examiner*—Perry E. Van Over
*Attorney, Agent, or Firm*—McAulayer Fisher Nissen Goldberg & Kiel, LLP

[57] ABSTRACT

A pull push device for removing a clot. The device includes an elongate tubular member having a suction port and an irrigation or fluid pressurization port respectively connectable to a vacuum source and a pressurizable fluid reservoir. The tubular member also has a clot intake port positionable through a patient's skin inside a clogged vascular vessel. The vacuum source enables clot suction into the clot intake port for severing while liquid pressure supplies fluid for clot ejection and device clearance. A single piece rotating or reciprocating cutter and intake closure component is mounted inside the tubular member for closing the clot intake port upon each small vacuum assisted severing of clot mass by the cutting element. By simultaneously severing the clot and closing the intake port by the closure component, the device automatically converts from a suction to a pressure mode, thus ejecting any clot through the suction port. The ordered and continual suck, cut, push, pull tandem ejection system is aided by an automatic anticlogging mechanism which is operative when a sucked clot obstructs suction through the tubular member. This self-limiting feature closes off further suction and ends the process of clot intake. Only after window closure and clot ejection has occurred is vacuum restored to the intake port so that more clot may be sucked into the device for processing.

45 Claims, 6 Drawing Sheets

U.S. PATENT DOCUMENTS

| | | |
|---|---|---|
| 4,678,459 | 7/1987 | Oink et al. . |
| 4,679,569 | 7/1987 | Olson . |
| 4,690,672 | 9/1987 | Veltrup . |
| 4,692,139 | 9/1987 | Stiles . |
| 4,729,763 | 3/1988 | Henrie . |
| 4,770,654 | 9/1988 | Rogers et al. . |
| 4,846,192 | 7/1989 | MacDonald . |
| 4,857,045 | 8/1989 | Rydell . |
| 4,890,611 | 1/1990 | Monfort et al. . |
| 4,890,612 | 1/1990 | Kensey . |
| 4,895,166 | 1/1990 | Farr et al. . |
| 4,898,575 | 2/1990 | Fischell et al. . |
| 4,909,249 | 3/1990 | Akkas et al. . |
| 4,909,781 | 3/1990 | Husted . |
| 4,911,161 | 3/1990 | Schechter . |
| 4,913,698 | 4/1990 | Ito et al. . |
| 4,921,476 | 5/1990 | Wuchinich . |
| 4,950,277 | 8/1990 | Farr . |
| 4,954,129 | 9/1990 | Giuliani et al. . |
| 4,966,604 | 10/1990 | Reiss . |
| 4,986,807 | 1/1991 | Farr . |
| 4,990,134 | 2/1991 | Auth . |
| 4,994,067 | 2/1991 | Summers . |
| 4,998,919 | 3/1991 | Schnapp-Pesch . |
| 5,002,553 | 3/1991 | Shiber . |
| 5,007,917 | 4/1991 | Evans . |
| 5,009,659 | 4/1991 | Hamlin et al. . |
| 5,011,488 | 4/1991 | Ginsburg . |
| 5,011,490 | 4/1991 | Fischell et al. . |
| 5,019,036 | 5/1991 | Stahl . |
| 5,019,088 | 5/1991 | Farr . |
| 5,030,201 | 7/1991 | Palestrant . |
| 5,042,984 | 8/1991 | Kensey et al. . |
| 5,052,999 | 10/1991 | Klein . |
| 5,069,224 | 12/1991 | Zinnanti . |
| 5,071,424 | 12/1991 | Reger . |
| 5,084,052 | 1/1992 | Jacobs . |
| 5,092,838 | 3/1992 | Kipperman . |
| 5,092,839 | 3/1992 | Kipperman . |
| 5,100,424 | 3/1992 | Jang et al. . |
| 5,102,415 | 4/1992 | Guenther et al. . |
| 5,114,399 | 5/1992 | Kovalcheck . |
| 5,135,483 | 8/1992 | Wagner et al. . |
| 5,135,484 | 8/1992 | Wright . |
| 5,192,268 | 3/1993 | Shiber . |
| 5,192,290 | 3/1993 | Hilal . |
| 5,192,291 | 3/1993 | Pannek, Jr. . |
| 5,242,404 | 9/1993 | Conley et al. . |
| 5,261,877 | 11/1993 | Fine et al. . |
| 5,269,751 | 12/1993 | Kaliman et al. . |
| 5,284,486 | 2/1994 | Kotula et al. . |
| 5,318,518 | 6/1994 | Plechinger et al. . |
| 5,322,504 | 6/1994 | Doherty et al. . |
| 5,342,377 | 8/1994 | Lazerson . |
| 5,348,535 | 9/1994 | Cucin . |
| 5,352,194 | 10/1994 | Greco et al. . |
| 5,356,375 | 10/1994 | Higley et al. . |
| 5,358,509 | 10/1994 | Fine et al. . |
| 5,370,609 | 12/1994 | Drasler et al. . |
| 5,370,653 | 12/1994 | Cragg . |
| 5,376,100 | 12/1994 | Lefebvre . |
| 5,395,313 | 3/1995 | Naves et al. . |
| 5,403,276 | 4/1995 | Schechter et al. . |
| 5,419,774 | 5/1995 | Willard et al. . |
| 5,429,136 | 7/1995 | Milo et al. . |
| 5,431,673 | 7/1995 | Summers et al. . |
| 5,453,088 | 9/1995 | Boudewijn et al. . |

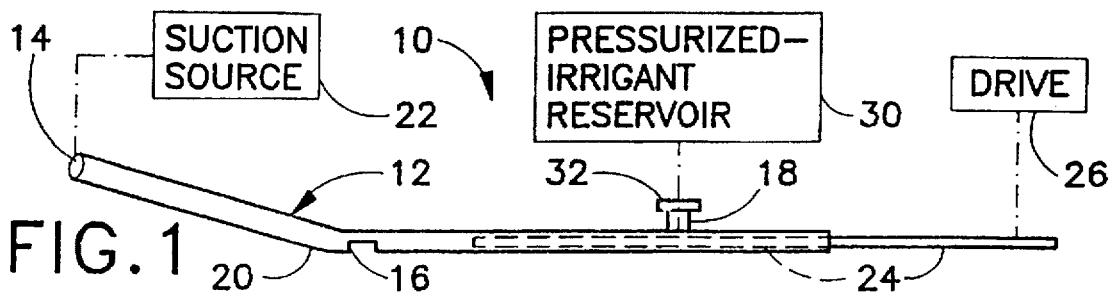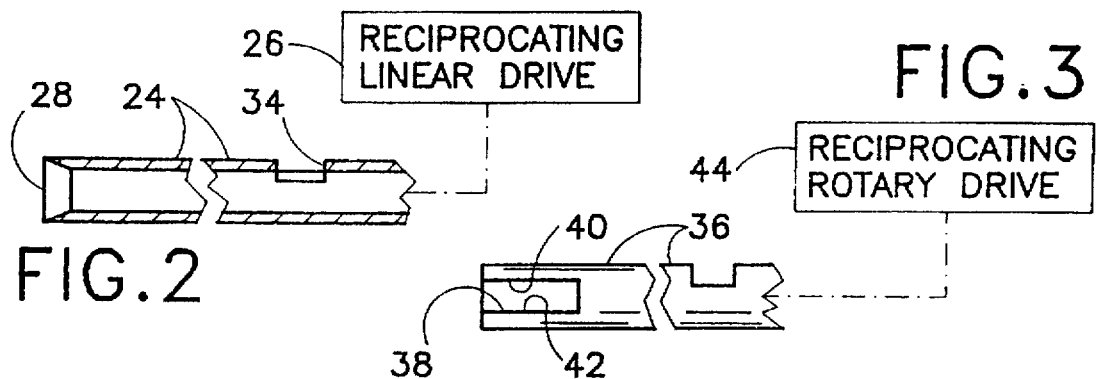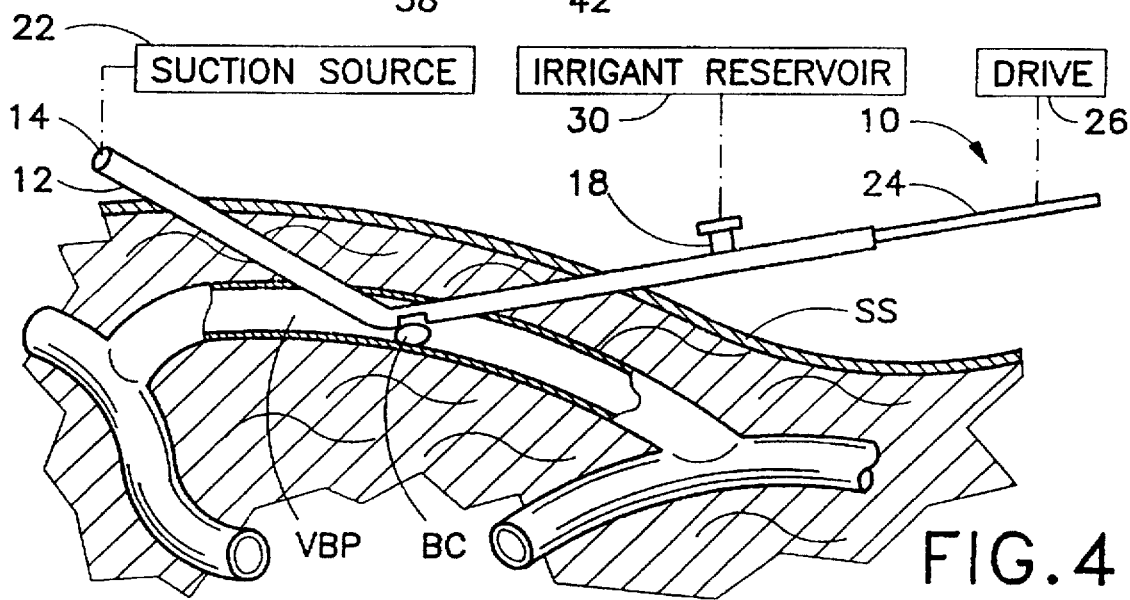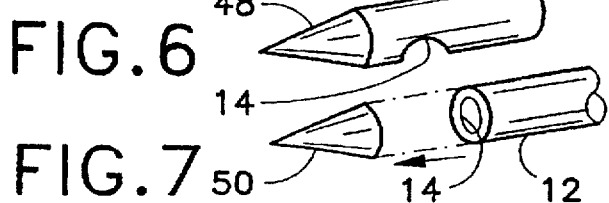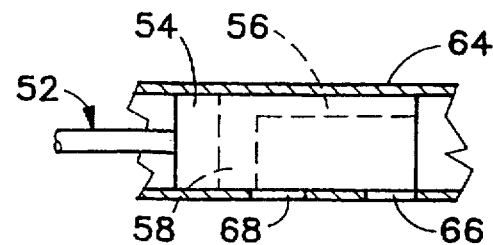

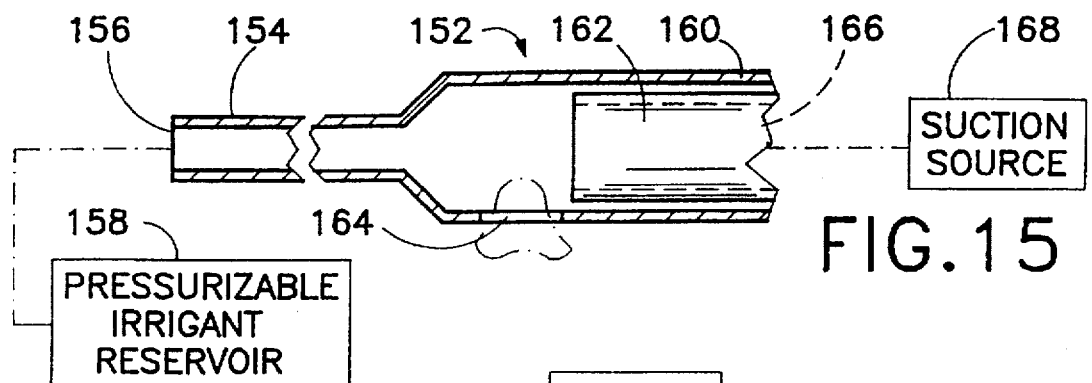
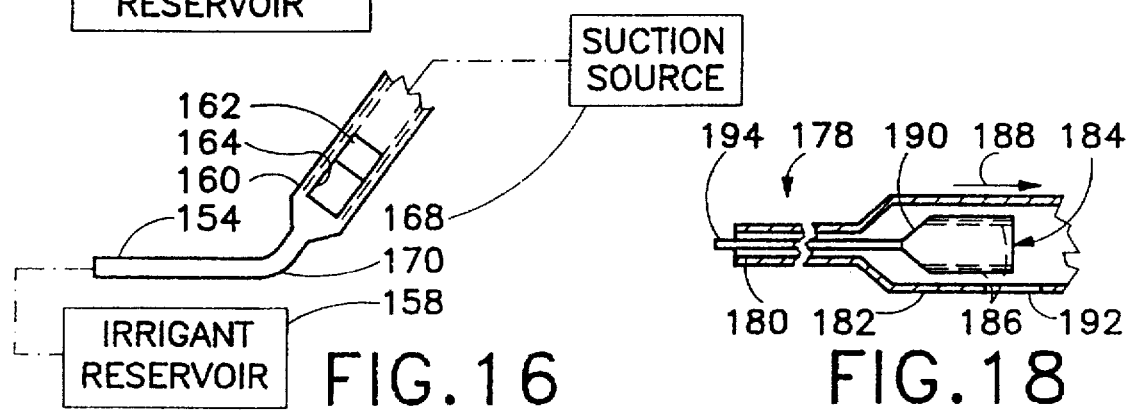
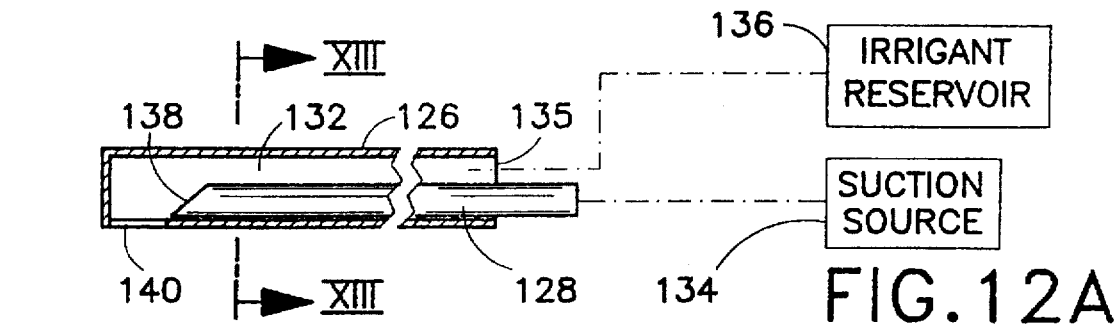
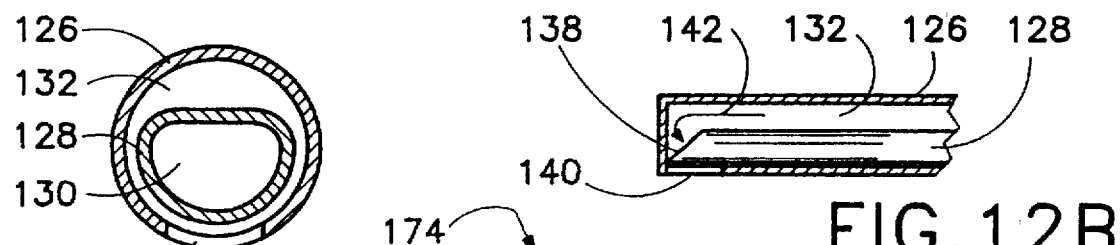
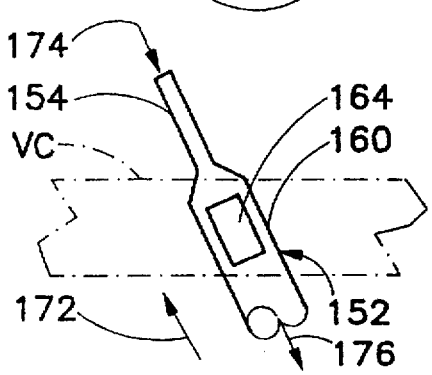

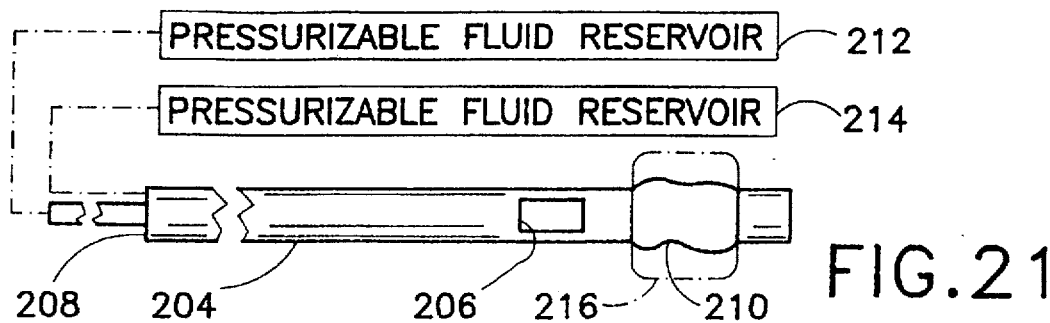
FIG. 21
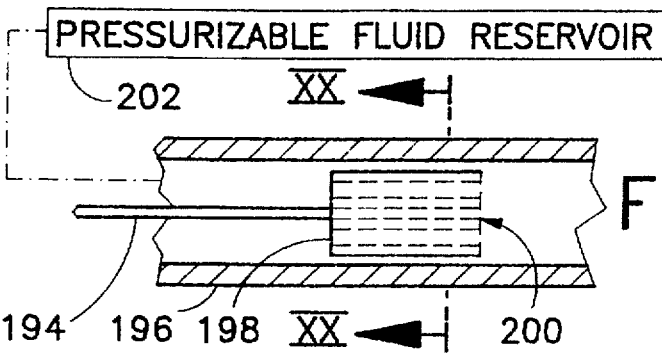
FIG. 19
FIG. 20
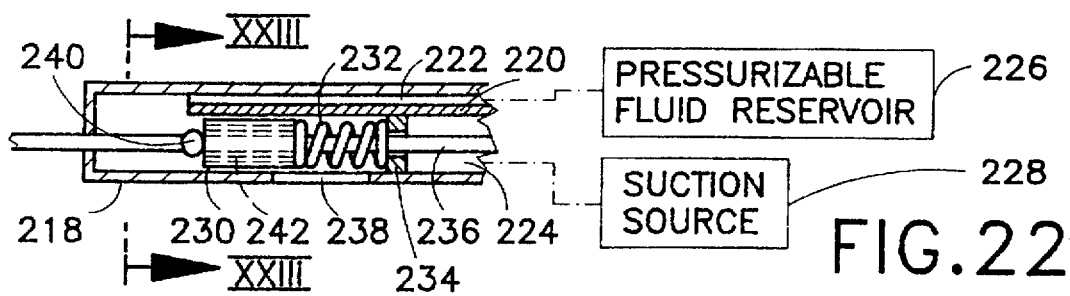
FIG. 22
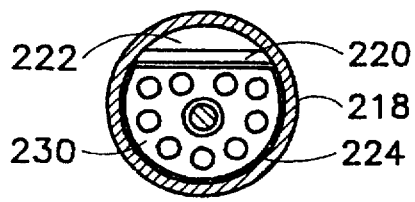
FIG. 23
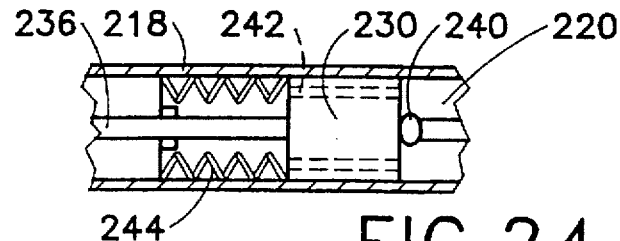
FIG. 24
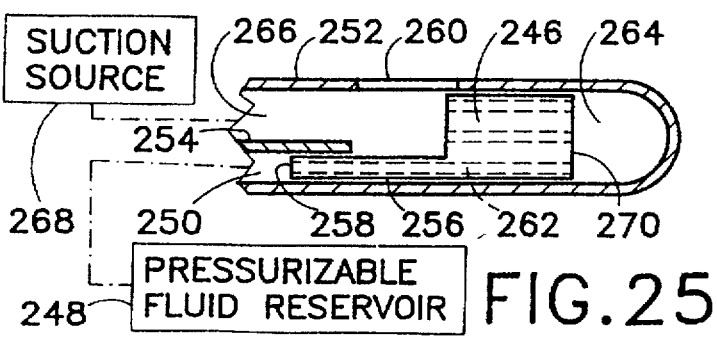
FIG. 25
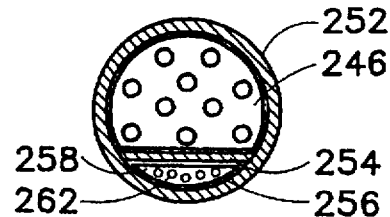
FIG. 26

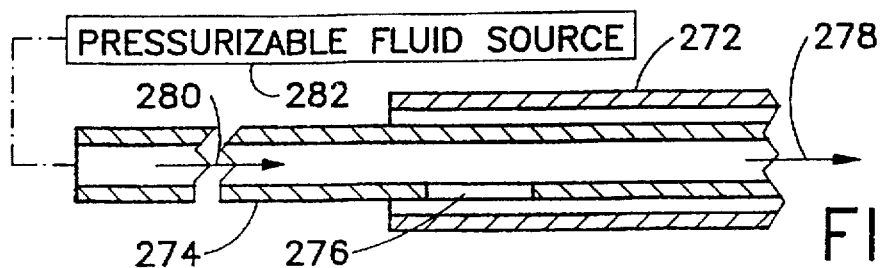
FIG. 27
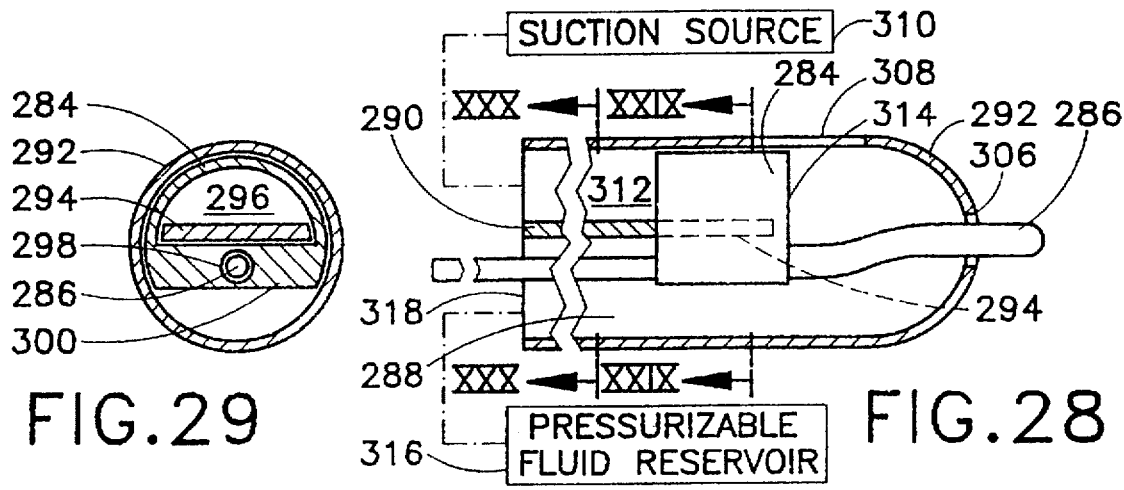
FIG. 29  FIG. 28
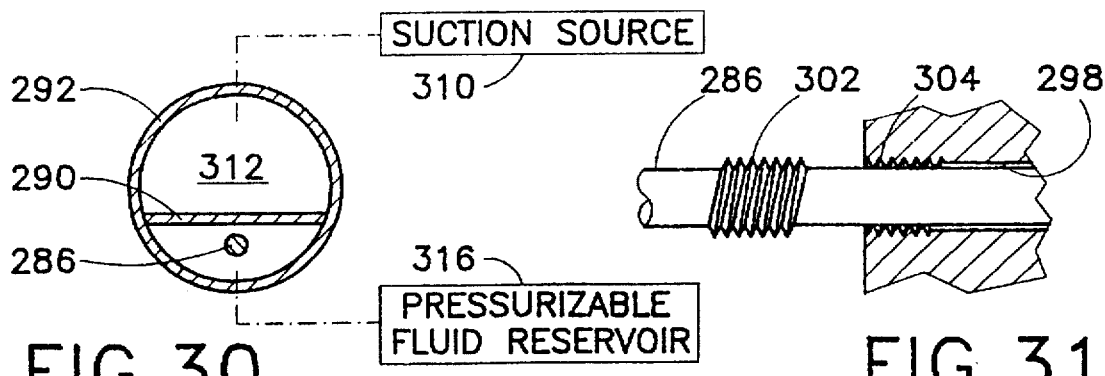
FIG. 30  FIG. 31
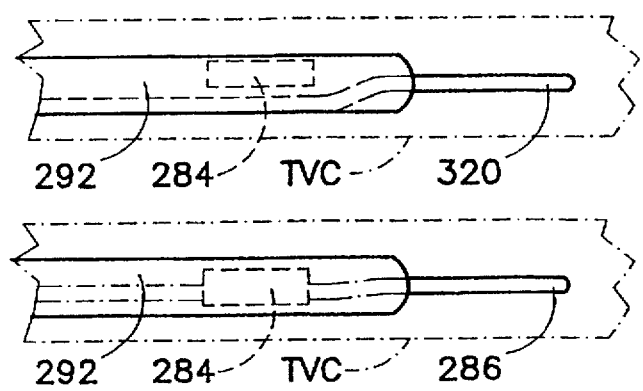
FIG. 32
FIG. 33

METHOD AND ASSOCIATED DEVICE FOR REMOVING MATERIAL FROM BODY

CROSS-REFERENCE TO RELATED APPLICATION

This application is a continuation-in-part of application Ser. No. 08/358,209 filed Dec. 16, 1994, now U.S. Pat. No. 5,520,635.

BACKGROUND OF THE INVENTION

This invention relates to a method and an associated device for removing material from a body or patient. The method and device are especially useful for removing clots from subcutaneous vascular bypasses or shunts.

Vascular bypasses, whether made of human (graft) tissue or polymeric material, become regularly blocked with blood clots which must be removed. A common technique for cleaning clogged vascular bypasses is surgical: the skin surface and the underlying shunt are cut open and instruments are inserted through the openings to extract clumps of clotted blood.

The disadvantages of this conventional surgical procedure are well known. Because of the blood which naturally spurts out through the incision, the cleaning of the graft or bypass must be performed in the operating room. Of course, all the disadvantages or side-effects of surgery pertain: pain to the patient, danger of infection, loss of blood, as well as time and expense due to the requisite hospital staff.

Another common method of cleaning clogged vascular bypasses is dissolution of the clot via biological enzymes. The most common enzyme in current use is urokinase. The disadvantages of this method include high cost of the enzymes and a delay of as much as several hours while the enzyme acts on the clot. Systemic side effects of these enzymes, notably bleeding at other sites in the body due to unwanted yet uncontrolled dissolution of other "good" clots, are also seen.

Other devices have attempted to clear clot from these vessels via mechanical percutaneous means. These devices, however, macerate the clot external to the device and frequently such macerated clot may not be captured and extracted from the body. In such cases, embolization to the lungs and other organs may occur. Biochemical aberrations secondary to clot and red blood cell emulsification by high powered devices may also occur.

OBJECTS OF THE INVENTION

An object of the present invention is to provide a new technique, and an associated instrument, for removing a vascular clot or other intravascular debris.

A more particular object of the present invention is to provide such a technique and associated instrument for removing a vascular clot or other intravascular debris in a subcutaneous vascular bypass or shunt which connects an artery with a vein to facilitate hemodialysis.

Another object of the present invention is to provide an associated instrument or device for performing the technique.

A further object of the present invention is to provide such a technique which reduces, if not eliminates, at least one or more disadvantages of conventional surgical or enzymatic clot removal techniques.

Another, more particular, object of the present invention is to enable the removal of high viscosity clots using tubes of small diameter.

Yet another particular object of the present invention is to provide such a technique or method which reduces the time required to remove a subcutaneous vascular clot.

These and other objects of the present invention will be apparent from the drawings and detailed descriptions herein.

SUMMARY OF THE INVENTION

A device for removing material from inside a patient comprises, in accordance with the present invention, an elongate tubular member having a suction port, an irrigation port and an intake port, with the suction port and the irrigation port being spaced from the intake port. A vacuum generator is operatively connected to the suction port for applying suction to the tubular member. A cutting element is mounted to the tubular member for severing a portion of material (e.g., clot) drawn partially in through the intake port upon disposition of the tubular member through a skin surface so that the suction port and the irrigation port are located outside the patient while the intake port is located in an internal organ of the patient. Fluid pressurization componentry is operatively connected to the tubular member for feeding a fluid thereto to pressurize the tubular member to eject the portion of the material severed by the cutting element. A closure, e.g., a reciprocating or rotating closure, is mounted to the tubular member for closing the intake port upon a severing of the portion of the material by the cutting element and prior to ejection of the severed material by the fluid pressurization componentry.

The cutting element may be movably, i.e., rotatably and/or slidably mounted to the tubular member, whereas the closure includes a surface of the cutting element.

Pursuant to another feature of the present invention, the fluid pressurization componentry includes means for feeding the pressurizing fluid past the cutting element. The cutting element may be provided with a fluid-flow channel so that fluid fed by the fluid pressurization componentry flows through the cutting element.

Where the tubular member is cylindrical, the cutting element may have a D-shaped cross-section defining two parallel D-shaped channels. The fluid pressurization componentry includes at least one of those channels.

The suction port and the irrigation port may be located on opposite sides of the intake port. As discussed below, where this embodiment of the invention is used, the suction and irrigation ports are disposed outside the patient while the intake port is disposed inside the patient during a thrombectomy or other material removal procedure.

Pursuant to a further feature of the present invention, a balloon is mounted to an external surface of the tubular member and means are connected to the balloon for alternately inflating and deflating the balloon.

Pursuant to a specific feature of the present invention, the cutting element may have an internally threaded bore, while a guidewire having an externally threaded segment is connected to the cutter element via the internally threaded bore and the externally threaded segment. The use of this embodiment of the invention is described below.

Pursuant to yet another feature of the present invention, the tubular member is provided on an inner surface with a constricting sleeve, while the cutter element is provided with a projection at a downstream end. The projection is insertable into the sleeve after a shifting of the cutter element past the intake port, to seal the device and then both mechanically and hydraulically push a severed mass through the sleeve and reduce the mass in size prior to an ejection thereof by the fluid pressurization componentry.

The cutting element may be spring loaded or shiftable under the action of fluid pressure.

A method for removing a clot in accordance with the present invention utilizes an elongate tubular member having a suction port, an irrigation port and an intake port, the suction port and the irrigation port being spaced from the intake port. The method comprises inserting a portion of the tubular member through a skin surface of a patient and into an internal organ such as a subcutaneous vascular component so that the suction and irrigation ports are located outside of the patient and the intake port is located in the internal organ. Upon completion of the insertion, suction is applied to the suction port of the tubular member to thereby draw material in the internal organ towards intake port of the tubular member. Then a portion of the material sucked inside the tubular member is severed as the device is sealed and fluid pressure is applied to the severed material to push the severed material along and ultimately out through the suction section of the tubular member.

Preferably, the application of fluid pressure is implemented in part by closing the intake port in the tubular member and feeding a fluid stream to the tubular member. The fluid stream is more preferably fed to the tubular member simultaneously with the closing of the intake port.

Where the tubular member is provided with a rotating or reciprocatable cutter element, the severing of the sucked-in material includes shifting the cutter element so that a cutting edge of the cutter element moves past the intake port of the tubular member, while the closing of the intake port includes blocking the intake port with the cutter element.

The pressurizing fluid fed to the tubular member for ejecting the severed mass may flow through the tubular member past the cutter element. Where the cutter element is provided with a fluid-flow channel, the application of fluid pressure includes feeding fluid through the channel.

In practice, fluid pressure need not be applied to every severed mass during a material removal operation (e.g., a thrombectomy). However, during every thrombectomy, a severed clot mass will become lodged in the tubular member, thereby blocking the tubular member and preventing further clot removal until the blocking clot mass is removed. In accordance with the present invention, such a stuck clot mass is forcibly ejected by applying a spike of fluid pressure. The generation of a sufficiently high clot ejection pressure is facilitated, particularly in thin tubular members, by the closing of the intake port (the intake port). Although closure of the intake port may be effectuated by a separate door element, the closure is advantageously effectuated by the cutter element itself. Such a solution reduces the number of parts and enables a maximal reduction in the size of the tubular member. The smaller the diameter of the tubular member the better, for example, for purposes of speeding the healing of the resulting smaller puncture ports in the patient's skin.

Where the tubular member is cylindrical, the cutter element may have a D-shaped cross-section defining two parallel D-shaped channels. In that case, the application of fluid pressure includes the feeding of fluid into one of the channels.

The application of fluid pressure to the tubular member to eject a severed mass generally includes the steps of connecting a pressurizable fluid source to the tubular member and feeding fluid under pressure from the source and at least partially along the tubular member past the intake port. Where the tubular member is provided with a cutter element, the fluid path extends past the cutter element, while the severing of sucked-in material includes shifting or rotating a cutting edge of the cutter element past the intake port. Where the cutter element is provided with a fluid-flow channel, the fluid path extends through the channel.

Preferably, a procedure in accordance with the present invention further comprises the step of applying suction to the tubular member at a point downstream of the intake port to pull the severed mass from the intake port along the tubular member.

Where the irrigation port and the suction port are disposed on opposite sides of the intake port, the inserting of a portion of the tubular member includes inserting a selected end of the tubular member through a skin surface of a patient into the internal organ (e.g., vascular component) and subsequently out of the internal organ and the skin surface so that the suction port and the irrigation port are located outside the patient while the intake port is located in the internal organ.

According to another feature of the present invention, the method further comprises (a) inserting a catheter with an inflatable balloon in a deflated configuration into the internal organ, (b) subsequently inflating the balloon, and (c) after inflation of the balloon, pulling the catheter and the balloon along the internal organ towards an insertion point of the tubular member into the internal organ, whereby clot material is shifted through the internal organ toward the intake port.

Where an end segment of the tubular member is inserted into the internal organ of the patient, the tubular member may be longitudinally shifted through or along the internal organ to remove material along an extended portion of the internal organ. In this particular embodiment of the present invention, it is frequently advantageous if at least a substantial part of the tubular member is made of a flexible material, so that the longitudinal shifting of the tubular member may include bending the tubular member. This feature is advantageous where the internal organ is in the vascular system of the patient. The bending allows the device to follow curves in the vascular system.

It is to be noted that a tubular member used in a method in accordance with the present invention may be completely rigid, partially rigid and partially flexible, or substantially entirely flexible. Generally, at least the cutter element and a section of the tubular member about the cutter element is rigid. This rigid section may be a small part of the entire tubular member. Where the entire tubular member is rigid, it is useful in a procedure where the tubular member has three ports as described above.

According to an additional feature of the present invention, the tubular member is provided with a cutter element having an internally threaded bore. Then the method further comprises inserting a first guidewire into an internal organ such as a vascular component prior to insertion of the tubular member, the insertion of the tubular member including inserting the tubular member into the vascular component along the guidewire. After insertion of the tubular member into the vascular component, the guidewire is removed. After removal of the first guidewire from the tubular member, a second guidewire having an externally threaded segment is inserted into the tubular member. Upon insertion of the second guidewire into the tubular member, the threaded segment of the guidewire is screwed to the threaded bore to thereby attach the second guidewire to the cutter element. After attachment of the second guidewire to the cutter element, the second guidewire is moved to shift the cutter element past the intake port.

According to a further feature of the present invention, where the tubular member is provided on an inner surface with a constricting sleeve and is further provided with a cutter element having a projection at downstream end, the projection is moved into the sleeve after shifting of a cutting edge of the cutter element past the intake port. The projection on the cutter element and the sleeve cofunction to squeeze a severed clot mass into a reduced size prior to a pushing of the severed portion of the clot along the tubular member by fluid pressure or fluid stream. The projection at the downstream end of the cutter element may define a shoulder on the cutter element which crushes severed clot mass against a ledge on the sleeve. This action further macerates severed clot mass and assists in facilitating the removal of severed clot material from the tubular member. It is to be noted that the cutter element in this case may be provided with one or more fluid flow channels of small diameter for generating fluid jets which serve to further macerate or particulize severed clot material.

Where the tubular member carries a reciprocatable cutter element provided with spring loading, the severing of clot mass including shifting the cutter element in a first direction so that a cutting edge of the cutter element moves past the intake port, while the method further comprises shifting the cutter element in a second direction opposite the first direction after a severing of the portion of the clot. The shifting of the cutter element in at least one of the first direction and the second direction is performed under action of the spring loading. Alternatively, in the absence of spring loading, the shifting of the cutter element in the first and/or the second direction may include the application of fluid pressure to the cutter element. For example, an oscillating pressure may be applied to a tongue or finger of the cutter element disposed inside a pressure channel in the tubular member. The cutter element reciprocates under the action of the oscillating pressure.

The present invention provides a technique and an associated device for removing material in an internal organ of a patient, such as a clot in a subcutaneous vascular bypass. The technique reduces, if not eliminates, one or more disadvantages of conventional surgical clot removal techniques. For example, the technique reduces the time required to remove surgically a subcutaneous vascular clot. Reduced time means less blood loss and reduced surgical costs. The technique also requires less time than enzymatic treatment and eliminates the expense of costly enzymes.

It is to be noted, that a prosthetic device implanted inside a patient is considered an internal organ for purposes hereof. For example, a vascular bypass made of synthetic materials is considered to be an organ for purposes of the present invention.

Furthermore, as compared to other clot disruption devices, this device only processes clot after the clot has been moved internal to the device via the associated suction capabilities. Only then is a portion of the clot severed and ejected, without any possibility of loss into the patient's vascular system. The remaining clot in the vascular vessel as yet unprocessed is not affected in any way by the device.

A clot removal device in accordance with the present invention entails a self-limiting anti-clogging system that inherently slows or stops the intake procedure concurrently with any clot buildup in the suction section of the clot ejection path of the tubular member. This anti-clogging feature does not interfere with the ongoing fluid pressure cleaning and ejecting system.

A clot removal device in accordance with the present invention may be used to remove material other than clots from organs other than blood vessels and vascular prostheses. The device may be used, for example, to remove malignant tissue from the liver or other solid organ (device inserted through vascular system or directly from overlying skin surface).

A device in accordance with the present invention can also be used in conjunction with or as a part of a cutting, scraping, shaving or other instrument in various internal organs, to clear suction ports or channels which frequently become clogged and otherwise would necessitate removal and cleaning. Many instruments use novel techniques to accomplish their stated goals. They all, however, generate debris which may be subsequently processed for ejection from the body through a smaller channel or whith a larger particle size than would otherwise appear possible. This enhanced two stage process, using another instrument and then a device as described herein for debris removal, would permit greater efficiency and improve the safety of these other instruments by quickly opening clogged suction channels and rapidly ejecting debris from the various organ systems.

It is to be noted further that interal organs of a patient may be protected from high ejection pressures by generating the high pressures only upon closure of the clot-intake port.

BRIEF DESCRIPTION OF THE DRAWING

FIG. 1 is partially a schematic side elevational view and partially a block diagram of a device for removing a subcutaneous blood clot, in accordance with the present invention.

FIG. 2 is partially a schematic longitudinal cross-sectional view and partially a block diagram showing a cutting component of the device of FIG. 1.

FIG. 3 is partially a schematic side elevational view and partially a block diagram showing an alternative cutting component for the device of FIG. 1.

FIG. 4 is partially a schematic cross-sectional view of subcutaneous tissues and a vascular bypass and partially a schematic side elevational view of the device of FIG. 1, showing a step in an operation removing a clot in the bypass.

FIGS. 5–7 are schematic partial perspective views of respective alternative embodiments of the distal end of tubular member 12, on an enlarged scale.

FIG. 8 is a schematic partial cross-sectional view of a modified obturator in accordance with the present invention.

FIG. 12A is partially a block diagram and partially a schematic partial longitudinal cross-sectional view, on an enlarged scale, of another thrombectomy device in accordance with the present invention, showing the device in a clot intake phase of an operating cycle.

FIG. 12B is a view similar to FIG. 12A, showing the device of FIG. 12A upon completion of a cutting or macerating stroke.

FIG. 13 is a schematic cross-sectional view taken along line XIII—XIII in FIG. 12A.

FIG. 15 is partially a block diagram and partially a schematic partial longitudinal cross-sectional view, on an enlarged scale, of a further thrombectomy device in accordance with the present invention.

FIG. 16 is a schematic side elevational view, on an enlarged scale, of a modification of the thrombectomy device of FIG. 15.

FIG. 17 is a diagram illustrating use of the thrombectomy device of FIG. 15 or 16.

FIG. 18 is a schematic partial longitudinal cross-sectional view, on an enlarged scale, of an additional thrombectomy device in accordance with the present invention.

FIG. 19 is partially a block diagram and partially a schematic partial longitudinal cross-sectional view, on an enlarged scale, of a modified thrombectomy device in accordance with the present invention.

FIG. 20 is a schematic transverse cross-sectional view taken along line XX—XX in FIG. 19.

FIG. 21 is schematic side elevational view, on an enlarged scale, of yet another thrombectomy device in accordance with the present invention.

FIG. 22 is partially a block diagram and partially a schematic partial longitudinal cross-sectional view, on an enlarged scale, of yet another thrombectomy device in accordance with the present invention.

FIG. 23 is a schematic transverse cross-sectional view taken along line XXIII—XXIII in FIG. 22.

FIG. 24 is a schematic partial longitudinal cross-sectional view showing a variation on the thrombectomy device of FIGS. 22 and 23.

FIG. 25 is partially a block diagram and partially a schematic partial longitudinal cross-sectional view, on an enlarged scale, of yet a further thrombectomy device in accordance with the present invention.

FIG. 26 is a schematic transverse cross-sectional view taken along line XXVI—XXVI in FIG. 25.

FIG. 27 is a schematic partial longitudinal cross-sectional view, on an enlarged scale, of a thrombectomy device in accordance with the present invention.

FIG. 28 is partially a block diagram and partially a schematic partial longitudinal cross-sectional view, on an enlarged scale, of another thrombectomy device in accordance with the present invention.

FIG. 29 is a schematic transverse cross-sectional view taken along line XXIX—XXIX in FIG. 28.

FIG. 30 is a schematic transverse cross-sectional view taken along line XXX—XXX in FIG. 28.

FIG. 31 is a partial cross-section view of a cutting element and wire shown in FIGS. 28 and 29.

FIGS. 32 and 33 are diagrams depicting different steps in the use of the thrombectomy device of FIGS. 28–31.

DETAILED DESCRIPTION

Figure 9:
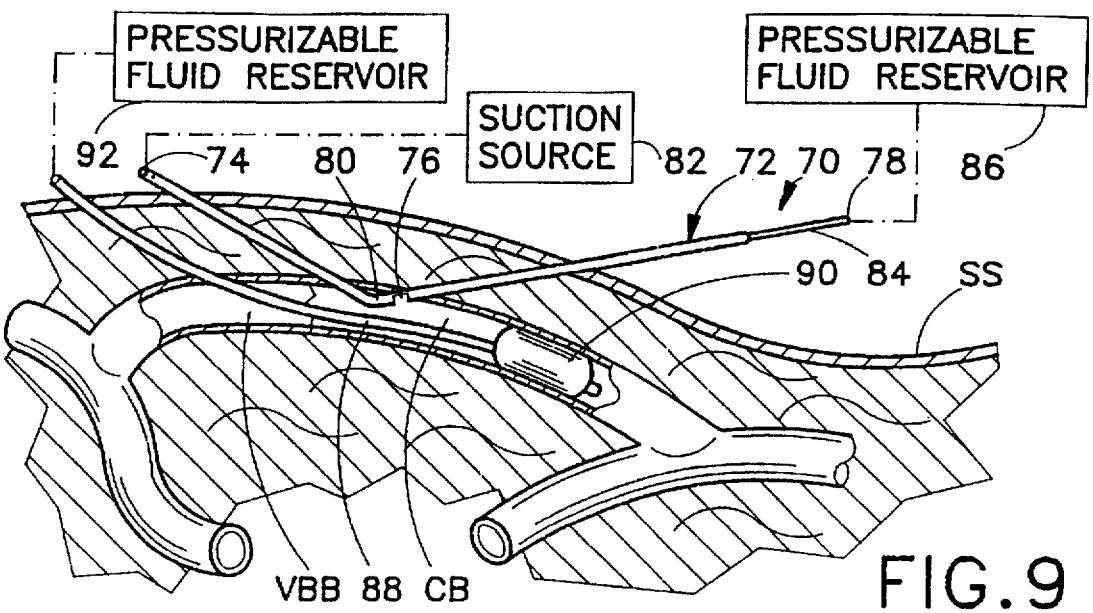
FIG. 9 is partially a schematic cross-sectional view of subcutaneous tissues and a vascular bypass and partially a schematic side elevational view of a device similar to that of FIG. 1, showing a modified clot removal technique in accordance with the present invention.

As illustrated in FIG. 1, a surgical instrument or device 10 for removing a blood clot from a patient comprises an elongate tubular member 12 having a most distal first port 14, an intermediately located second port 16 and a most proximal third port 18 all spaced from each other along the tubular member. Tubular member 12 is provided with a bend or elbow 20 for facilitating the insertion of the distal end portion of the instrument into a patient so that distal port 14 and proximal port 18 both lie outside the patient, while intermediate port 16 lies inside a subcutaneous blood vessel, graft or vascular bypass VBP (FIG. 4).

A vacuum generator or suction source 22 is operatively connected to distal port 14 for applying suction to tubular member 12. A hollow obturator 24 is shiftably inserted inside tubular member 12. At a proximal end, obturator 24 is operatively connected to an automatic reciprocating linear or translatory drive 26, while at a distal end the obturator 24 is provided with a circular blade or cutting edge 28 (FIG. 2). Drive 26 reciprocates obturator 24 back and forth across intermediate port 16. Upon a retraction stroke, intermediate port 16 is uncovered by obturator 24 to permit suction from suction source 22 to draw a blood clot BC in bypass VBP partially into the tubular member 12 through intermediate port 16 (see FIG. 4). A subsequent distally directed stroke of obturator 24 pushes cutting edge 28 against blood clot BC, thereby severing or macerating a portion thereof.

As further illustrated in FIG. 1, a supply or reservoir 30 is operatively connected via a luer lock or similar function adapter 32 to proximal port 18 for feeding a saline irrigation fluid to tubular member 12 upon a severing of a portion of blood clot BC by cutting edge 28 of obturator 24. The forward pushing motion of obturator 24 serves in part to assist the pulling action of suction source 22 to remove the severed clot portion from tubular member 12. A greater push is provided, however, by the saline irrigant from supply or reservoir 30. The irrigant is placed under pressure to facilitate the removal of severed clot portions from tubular member 12.

Obturator 24 is provided with an aperture 34 spaced from cutting edge 28 by approximately the same distance as that between intermediate port 16 and proximal port 18. Thus, upon a severing of blood clot BC during a distally directed stroke of obturator 24, obturator 24 is connected to pressurized irrigant reservoir 30 via proximal port 18 and aperture 34, thereby providing a timely flow of irrigant to force the severed clot material from tubular member 12. This pushing action is believed to so facilitate the removal of severed clot material that obturator 24 and tubular member 12 can be constructed with diameters thinner than those which might have only suction forces to remove severed clot material. Accordingly, small diameter tubes may be used to remove clots of relatively high density.

Aperture 34 and proximal port 18 cofunction as a valve to permit the flow of irrigant only upon a severing of a blood clot BC by cutting edge 28 of obturator 24. During the pressurization of obturator 24 by the irrigant from reservoir 30, obturator 24 is juxtaposed to intermediate port 16 so as to prevent the flow of pressurizing fluid into bypass VBP. This juxtaposition occurs periodically inasmuch as the invention contemplates an alternating cycle: initially a vacuum and other assist devices suck clots into the tubular clot-removal device. Only after that has been accomplished and the obturator changes position does the pressure cycle commence during which the obturator and/or pressurized saline solution ejects the clot material.

As shown in FIG. 2, cutting edge 28 is a circular edge provided by beveling obturator 24 at a distal end thereof.

As shown in FIG. 3, an obturator element 36 insertable inside tubular member 12 is provided at a distal end with a longitudinally extending slot 38 formed along longitudinal edges with blades 40 and 42 for alternately slicing off portions of a blood clot sucked into tubular member 12 through intermediate port 16 by operation of suction source 22. Obturator element 36 is operatively connected at a proximal end to a reciprocating rotary drive 44. Drive 44 functions to shift blades 40 and 42 alternately past intermediate port 16.

It is to be noted that rotary drive 44 may be sufficient to macerate a clot to a particle size suitable for evacuation through tubular member 12 by suction. However, obturator element 36 may be additionally connected to a reciprocating drive for facilitating clot particle ejection or removal. Pressurized saline may or may not be provided. The requirements will vary depending on the characteristics of the particular clots.

As depicted in FIG. 4, a distal end of tubular member 12 is inserted through a skin surface SS of a patient into a subcutaneous tubular vascular component in the form of bypass VBP and subsequently out of bypass VBP and skin surface SS so that distal port 14 and proximal port 18 are located outside the patient while intermediate port 16 is located in bypass VBP. Upon completed insertion of the device, suction source 22 is operated to apply suction to distal port 14 to thereby draw blood clot BC in bypass VBP towards intermediate port 16. Upon a drawing of the clot at least partially into tubular member 12 through intermediate port 16, a portion of the clot is severed inside tubular member 12 by a distally directed stroke of obturator 24 or an angular shifting of obturator element 36. Subsequently, the severed clot portion is removed from tubular member 12 through distal port 14, in part because of the feeding of irrigant under pressure from reservoir 30 and in part because of the suction applied by source 22.

It is to be noted that the present invention is used in conjunction with conventional mechanical surgical techniques for drawing clot material from opposite ends of bypass VBP towards intermediate port 16. For example, a wire (not illustrated) inserted through the same or a different puncture site may be manipulated to catch clotted clumps of blood and drag the captured clumps towards intermediate port 16 where the clumps are subjected to a suction force tending to draw the clot material into intermediate port 16. Also, Fogarty balloon catheters (not illustrated) may be used to push the clots, or another catheter (not illustrated) may inject fluid under pressure into the bypass graft to enhance further the flow of the clot to intermediate port 16 and out through tubular member 12.

FIGS. 5–7 illustrate respective alternative embodiments of the distal end of tubular member 12. As shown in FIG. 5, a sharp point 46 for skin penetration is provided by beveling the entire distal end of tubular member 12. Alternatively, as depicted in FIG. 6, the distal most port 14 in tubular member 14 is spaced from a sharpened distal tip 48 of the tubular member. As illustrated in FIG. 7, a tapered or sharpened distal tip 50 of tubular member 12 may be severed or otherwise separated from the rest of the tubular member, thereby forming port 14.

As shown in FIG. 8, an obturator 52 extending through a vascular access tube 64 as described hereinabove may have a substantially solid distal end portion 54. That end portion 54 is formed with a groove 56 and a passageway 58 for enabling the transmission of irrigant from a proximal most port 68 in a distal direction upon the completion of a cutting stroke of obturator 52 at an intermediate port 66. Alternatively, a solid, but loosely fitting, obturator may be used, where pressurized irrigant flows around the obturator.

FIG. 9 illustrates a stage in a thrombectomy procedure utilizing a clot removal instrument or device 70. As described hereinabove with reference to FIG. 1, device 70 comprises an elongate tubular member 72 having a most distal first port 74, an intermediately located second port 76 (suction intake port) and a most proximal third port 78 all spaced from each other along the tubular member. Tubular member 72 is provided with a bend or elbow 80 for facilitating the insertion of the distal end portion of the instrument into a patient so that distal port 74 and proximal port 78 both lie outside the patient, while intermediate port 76 lies inside a subcutaneous blood vessel, graft or vascular bypass VBB.

A vacuum generator or suction source 82 is operatively connected to distal port 74 for applying suction to tubular member 72. A hollow obturator 84 is shiftably inserted inside tubular member 72. At a proximal end, obturator 84 is operatively connected to a pressurizable fluid reservoir 86 such as a syringe, while at a distal end the obturator 84 is provided with a cutting edge or blade (not shown in FIG. 9). Obturator 84 is manually reciprocated inside tubular member 72. Upon a distally directed cutting stroke of obturator 84, a portion of a blood clot CB sucked into tubular member 72 through port 76 is severed. In addition, cutting element or obturator 84 blocks port 76, thereby enabling or facilitating the forcible ejection of the severed blood clot mass from port 74 by the application of fluid pressure to tubular member 72 upon a pressurization of fluid reservoir 86. Upon a subsequent retraction stroke of cutting element or obturator 84, clot intake port 76 is uncovered by obturator 84 to permit suction from suction source 82 to draw another portion of blood clot CB in bypass VBB partially into the tubular member 72 through intermediate port 76. A subsequent distally directed stroke of obturator 84 pushes the cutting edge thereof against blood clot CB, thereby severing or macerating a portion thereof. Again, as described hereinabove with respect to FIG. 1, saline irrigant from reservoir 86 provides sufficient pressure to remove any severed clot mass which would otherwise become stuck inside tubular member 72.

As further illustrated in FIG. 9, a catheter 88 with a collapsed balloon 90 attached to an external surface may be inserted into the patient's vascular system, particularly into bypass VBB, so that the balloon is located on a distant side of the blood clot CB. A fluid reservoir 92 (e.g., syringe) is then pressurized to inflate balloon 90, as shown in FIG. 9. Subsequently, a traction force is placed on catheter 88 to drag blood clot CB along bypass VBB towards clot intake port 76 of instrument 70. This procedure facilitates removal particularly of a large clot CB.

Figure 10B:
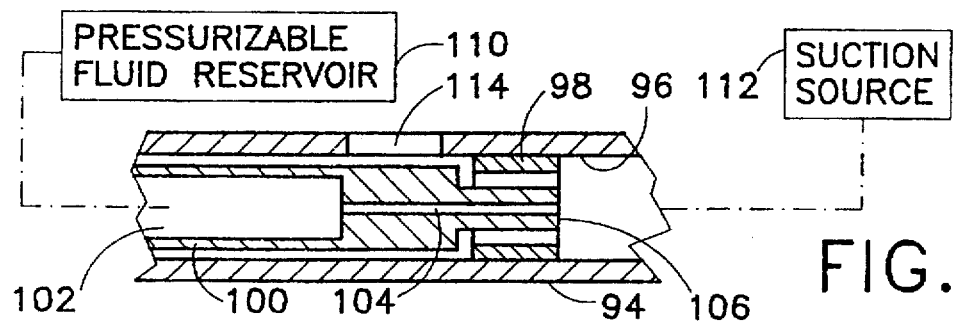
FIG. 10B is a view similar to FIG. 10A, showing the device of FIG. 10A in a cutting or macerating phase of an operating cycle.
Figure 10A:
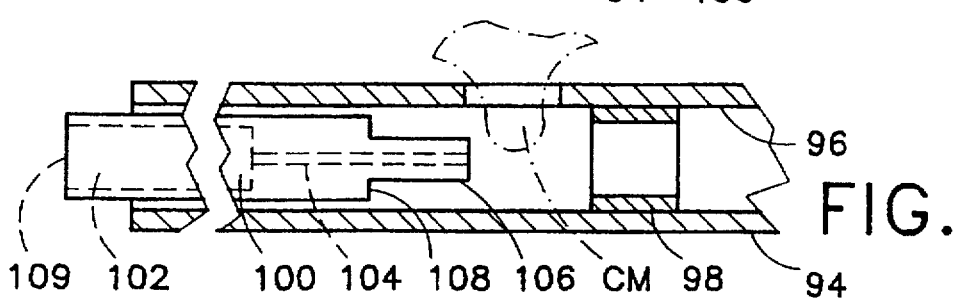
FIG. 10A is partially a block diagram and partially a schematic partial longitudinal cross-sectional view, on an enlarged scale, of a modified thrombectomy device in accordance with the present invention, showing the device in a clot intake phase of an operating cycle.

As depicted in FIGS. 10A and 10B, a modified thrombectomy device comprises a tubular member 94 provided on an inner surface 96 with a sleeve 98. A cutting element 100 in the form of an obturator has a longitudinally extending channel 102 with a narrowed distal end segment 104. The distal end of cutting element or obturator 100 is provided with an axially extending projection 106 which is insertable into sleeve 98 upon a distally directed cutting stroke of cutting element or obturator 100, as shown in FIG. 10B. Projection 106 partially defines a shoulder 108 which is engageable with sleeve 98. Channel 102 of cutting element or obturator 100 communicates at a proximal port 109 (FIG. 10A) with a pressurizable fluid reservoir 110 (FIG. 10B), while an end of tubular member 94 opposite cutting element 100 communicates with a suction source or vacuum generator 112.

Upon a drawing of a clot mass CM into tubular member 94 through a window or clot intake port 114 therein, a distally directed stroke of cutting element 100 severs the clot mass. The clot mass is forced by projection 106 through sleeve 98, thereby macerating or reducing the severed clot mass in size. This maceration or reduction in size further facilitates the removal of the severed clot mass from tubular member 94. The severed clot mass is also crushed (partially) between sleeve 98 and shoulder 108. In addition, the severed clot mass is subjected to a jet of saline irrigant (not shown) exiting cutting element 100 via narrowed distal end segment 104 of channel 102.

Figure 11:
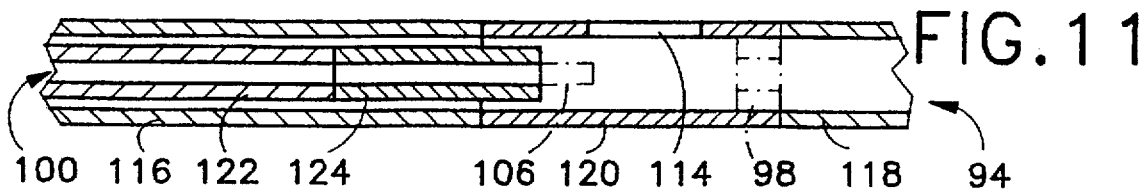
FIG. 11 is a schematic partial longitudinal cross-sectional view, on an enlarged scale, of a thrombectomy device similar to that of FIGS. 10A and 10B, showing particular implementations with respect to materials.

As illustrated in FIG. 11, tubular member 94 may be partially made of a flexible material. More particularly, tubular member 94 may include a flexible proximal section 116 connected to a flexible distal section 118 by a rigid section 120 which includes window or clot intake port 114. In this case, cutting element 100 has a flexible body 122 and a rigid tip 124. If sleeve 98 and projection 106 are not omitted, they are preferably provided on rigid section 120 and rigid tip 124, respectively.

The modified thrombectomy device of FIG. 11 is particularly useful in removing clots from blood vessels which do not lie near a skin surface. Rigid section 120 may be positioned proximally to an intravascular clot via well known guidewire techniques.

As depicted in FIGS. 12A, 12B, and 12C, another thrombectomy device comprises a tubular member 126 provided with a cross-sectionally D-shaped cutting element or obturator 128 which defines a suction channel 130 and a pressurization channel 132. Suction channel 130 is connected to a suction source or vacuum generator 134, while pressurization channel 132 is coupled at an irrigant inlet port 135 to a pressurizable irrigant or saline reservoir 136. At a distal end cutting element 128 is beveled to define a cutting edge or blade 138. Upon a distally directed stroke of cutting element 128 (compare FIGS. 12A and 12B), cutting edge 138 moves past a clot intake window or port 140 in tubular member 126 to sever a potion of clot projecting into the tubular member through window 140. In the event that the suction from source 134 is insufficient to pull the severed clot portion from tubular member 126, the pressure of fluid in reservoir 136 is increased. Cutting element remains in the position shown in FIG. 12B to thereby close or block window 140 and enable or facilitate a build-up of fluid pressure behind the severed clot mass sufficient to forcibly eject the clot mass from tubular member 126. As indicated by an arrow 142 in FIG. 12B, saline irrigant from reservoir 136 flows through irrigation channel 132 and around the beveled leading edge of cutting element 128 into suction channel 130.

Figure 14:
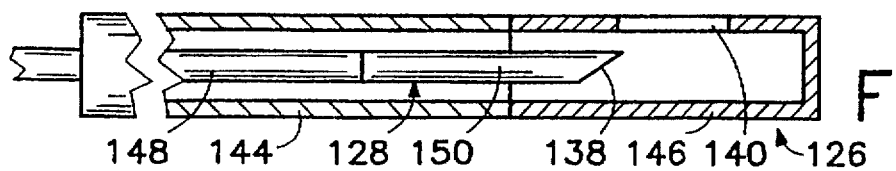
FIG. 14 is a schematic partial longitudinal cross-sectional view, on an enlarged scale, of a thrombectomy device similar to that of FIGS. 12A, 12B and 13, showing particular implementations with respect to materials.

As illustrated in FIG. 14, the thrombectomy device of FIGS. 12A, 12B and 13 may be partially flexible for insertion through arcuate blood vessels. More specifically, tubular member 126 may have a flexible body segment 144 and a rigid tip 146 provided with window 140. Similarly, cutting element or obturator 128 may have a flexible body segment 148 and a rigid tip 150 provided with cutting edge 138.

It is to be noted that in the thrombectomy probe embodiments of FIGS. 12A, 12B, 13 and 14, as well as in all of the other thrombectomy devices disclosed herein, the cutting element 128 has a cutting edge or blade 138 functioning to sever a clot mass pulled into tubular member 126 through intake port or window 140 and also has a surface (internal or external) which functions to close the window during a subsequent pressurization of the tubular member to eject a stuck clot therefrom. Although not every severed clot mass will require forcible ejection via hydrostatic pressurization or hydrodynamic forces, every thrombectomy procedure utilizing a thin tubular member as disclosed herein will require one or more applications of fluid pressure to hydrostatically or hydrodynamically eject a lodged clot mass from the tubular member.

As depicted in FIG. 15, another thrombectomy device comprises a tubular member 152 having a narrow section 154 connected at an irrigant inlet port 156 to a pressurizable reservoir 158 containing a saline solution or irrigant. Tubular member 152 has a wide section 160 in which a cutting element 162 in the form of an obturator is slidably disposed for motion past a clot intake window or port 164. Cutting element 162 is hollow, i.e., defines a fluid flow channel 166 which communicates with a suction source or vacuum generator 168. Cutting element 162 enters tubular member 152 at an opening (not shown) therein. FIG. 16 shows the thrombectomy device of FIG. 15 provided with a bend 170 in narrow section 154 proximate to wide section 160.

As indicated in FIG. 17, the thrombectomy device of FIG. 15 (or 16) is used by inserting narrow section 154 into a vascular component VC, as indicated by arrow 172, so that window 164 is disposed inside vascular component VC and so that the opposite ends of tubular member 152, as well as the irrigant inlet and suction ports thereof) are disposed outside the patient. Pressurizable irrigant is fed into tubular member 152 via narrow section 154, as indicated by an arrow 174, while macerated clot mass is removed via wide section 160 (arrow 176).

It is to be noted that irrigant from any pressurizable reservoir (e.g., syringe) disclosed herein may flow or leak at a low rate for lubrication purposes during unclogged operation of the respective thrombectomy device. When a severed clot mass becomes stuck in the tubular member, the pressure of the fluid irrigant is increased to impose an ejection force on the stuck clot mass.

In FIG. 18, a tubular member 178 of a thrombectomy device has a narrow irrigant inlet section 180 and a wide suction section 182. A cutter element 184 comprises a cylindrical segment perforated with a multiplicity of bores 186 so that the cutter element is moved in a cutting stroke, as indicated by an arrow 188, upon the application of fluid pressure to a conical rear surface 190 of the cutting element via narrow irrigant inlet section 180. After a severing of a clot mass (not shown) protruding into tubular member 178 via an opening, port or window 192 and after removal of the severed clot mass from the tubular member, a cable or wire 194 attached to cutter element 190 is pulled to return the cutting element to a precutting position in which window 192 is open for drawing in further clot mass.

In the embodiment of FIG. 18, as in essentially all the thrombectomy devices discussed herein, fluid pressure is used to eject any severed clot mass which becomes lodged in the tubular member. The cutting element is maintained in position over the clot intake window or port 192 to ensure the generation of sufficient pressure to eject the ledged clot material. In the embodiment of FIG. 18, a sleeve (not shown) may be provided in tubular member 178 downstream of window 192 to arrest downstream motion of cutting element 184 upon closure of window 192 thereby. Alternatively, wire 194 may be used to hold cutting element 184 in position during a clot ejection phase of a thrombectomy procedure. In any event, bores 186 are sufficiently small in total cross-sectional area to enable fluid pressure to push cutting element 184 past window 192, but sufficiently large in total cross-sectional area to enable pressurization of the tubular member for ejecting a stuck clot mass.

FIGS. 19 and 20 show a slight modification of the thrombectomy device of FIG. 18, in which a tubular member 196 has an essentially uniform diameter or cross-section and in which a rear surface 198 of a cylindrical cutting element 200 is planar rather than conical. A pressurizable fluid reservoir 202 is connected to tubular member 196 at an end opening or port (not shown) thereof. Otherwise, the essential structure and operation of the thrombectomy device of FIGS. 19 and 20 is the same as that of the thrombectomy device of FIG. 18, as indicated by the use of like reference designations.

FIG. 21 shows a generalized thrombectomy device with a tubular member 204, a clot intake port 206, and an irrigant port 208 at one end. In addition, an inflatable balloon 210 is provided on tubular member 204 for occluding a clotted vascular component and dragging a clot to a desired location in the vascular component for removal. It is to be understood that balloon 210 may be provided on any of the thrombectomy devices disclosed herein which are longitudinally shiftable along a clotted vascular component during a thrombectomy procedure. As additionally shown in FIG. 21, a first pressurizable fluid reservoir 212 is connected to a cutting obturator 214 slidably disposed inside tubular member 204. Pressurizable fluid reservoir 212 supplies a fluid to the tubular member for purposes of lubricating the sliding relationship between obturator 214 and tubular member 204 and for purposes of forcibly ejecting a stuck clot mass from tubular member 204. Another pressurizable fluid reservoir 214 communicates with balloon 210 via tubular member 204 for inflating the balloon as indicated at 216.

As illustrated in FIGS. 22 and 23, a spring loaded thrombectomy device comprises a tubular member 218 provided with a longitudinally extending partition 220 dividing the lumen of tubular member 218 into a fluid feed channel 222 and a suction channel 224. A pressurizable fluid reservoir 226 communicates with fluid feed channel 218, while a suction source or vacuum generator 228 communicates with suction channel 224, both at an opening or port (not shown) at a proximal end of tubular member 218. A cutting element 230 is slidably disposed in suction channel 224 at a distal end thereof and is biased in the distal direction by a helical compression spring 232 disposed between the cutting element and a sleeve 234 attached to partition 220 and to tubular member 218 along an inner surface thereof. A wire 236 extends through cutting element 230 and along suction channel 224 for pulling the cutting element in a proximal direction in opposition to a force exerted by spring 232, thereby moving cutting element 230 past a clot intake window or port 238 to sever an inwardly protruding clot mass and to close the window for enabling or facilitating a pressurized ejection of the severed clot mass. A ball 240 on wire 236 transmits force between wire 236 and cutting element 230. Cutting element 230 is provided with longitudinally extending bores 242 for delivering pressure fluid from a distal end of fluid feed channel 218 to suction channel 224 upstream of a stuck clot mass.

Fluid from reservoir 226 flows along a path extending through feed channel 218, through bores 242 in cutting element 230 and past window or port 238 into suction channel 224. In virtually all of the thrombectomy devices disclosed herein, pressure fluid flows such a path. Fluid pressure upstream of a clogging clot mass is augmented by the closing of the clot intake port by the cutting element.

FIG. 24 depicts a variation of the thrombectomy of FIGS. 22 and 23, in which helical compression spring 232 is replaced by a plurality of smaller compression springs 244 angularly spaced from one another about an inner surface of tubular member 218. Those skilled in the art can readily appreciate that other variations in the structure for reciprocating the cutting element may be derived. For example, instead of compression springs, tension springs might be used.

FIGS. 25 and 26 illustrate a thrombectomy device wherein reciprocation of a cutting element 246 is accomplished hydraulically. A saline fluid from a periodically pressurizable reservoir 248 is fed to an opening or port (not shown) at a proximal end of a fluid feed channel 250 defined in a tubular member 252 by a partition 254. Cutting element 246 has an elongate eccentrically disposed drive member 256 located along an inner surface of tubular member 252 and projecting into channel 250 at a distal end thereof, the drive member 256 having a pressure face 258 acted on by the fluid in channel 250. Upon a pressurization of channel 250, cutting element 246 moves in a distal direction, thereby uncovering a clot intake port 260 in tubular member 252. Fluid from channel 250 leaks though bores 262 provided in drive member 256 to a chamber 264 at a distal end of tubular member 252. Pressure in that chamber can be increased sharply to force cutting element 246 in the proximal direction, thereby severing any clot mass sucked into tubular member 252 through port 260 owing to a depressurization of a suction channel 266 by a suction source or vacuum generator 268. Cutting element 246 has a pressure face 270 which is greater in surface area than finger pressure face 258, whereby a force may be exerted on cutting element 246 to produce a cutting stroke. Pressure is reduced to enable a distally directed return stroke. Cutting element 246 is provided with additional bores to enable forcible clot mass ejection, as described above.

FIG. 27 illustrates, in generalized format, a thrombectomy device wherein a cutting element 272 is slidably disposed outside a tubular thrombectomy member 274 for motion past a clot intake port 276 to sever a clot mass (not shown) sucked into the tubular member through the port 276 and to temporarily cover the window during extraction of the clot at least by a suction force applied to one end of the instrument, as schematically indicated by an arrow 278. An irrigating or lubricating fluid is fed to tubular member 274, for example, from an opposite end thereof, as indicated by an arrow 280. In the event that the suction force is inadequate to extract the severed clot mass, the irrigant may be pressurized, e.g., by a syringe or other pressurizable fluid source 282, to forcibly eject the clot mass. The closing of port 276 by an inner surface of cutting element 272 enables or at least facilitates the generation of sufficient pressure to eject the severed clot mass.

It is to be noted that an external cutting element, as described with reference to FIG. 27, may be utilized in a thrombectomy device wherein pressure fluid is fed to the tubular member at the same end thereof to which a suction source is coupled. In that event, a partition divides the tubular member into a fluid feed channel and a suction channel. It is to be further noted that the pressure fluid flows along a path past the clot intake opening or port and through the cutting element. This is the case even where the cutting element extends from the irrigant inlet end (left side in FIG. 27).

In another embodiment of a thrombectomy device illustrated in FIGS. 28–31, reciprocating movement of a cutting element 284 is implemented via a stiff wire 286 which is connected to the cutting element, as described below. Wire 286 extends eccentrically along a fluid feed channel 288 defined by a partition wall 290 disposed along an inner surface of a tubular thrombectomy member 292. Partition wall 290 projects at a distal end 294 into a D-shaped channel 296 (FIG. 29) in cutting element 284.

As shown in FIGS. 29 and 31, wire 286 traverses a bore 298 (FIGS. 29 and 31) in a wall 300 (FIG. 29) of cutting element 284. Wire 286 is provided with an external screw thread 302 which threadingly mates with an internal screw thread 304 in bore 298. At a distal side of cutting element 284, wire 286 extends through an aperture 306 in tubular member 292.

During a thrombectomy operation, a clot mass is sucked into tubular member 292 through an opening or port 308 therein, through the operation of a suction source 310 connected to a proximal end of a suction channel 312 defined in tubular member 292 by partition wall 290. Wire 286 is then pushed in a distal direction to move cutting element 284 and particularly a cutting edge 314 thereof past opening or port 308. At least a portion of the severed clot mass is disposed inside channel 296 of cutting element 284. A suction force applied by suction source 310 via channel 312 pulls the severed clot mass through channel 296 in cutting element 284 and proximally through channel 312. In the event that the severed clot mass becomes lodged inside cutting element 284 or suction channel 312, a fluid reservoir 316 communicating with fluid feed channel 288 via an opening or port 318 is pressurized to build up a back pressure to forcibly eject the lodged clot mass from tubular member 292. Subsequently to the extraction of the severed clot mass from tubular member 292, wire 286 is pulled to move cutting element 284 back in the proximal direction to uncover opening 318 and thereby initiate another cutting cycle.

As depicted diagrammatically in FIG. 32, the thrombectomy device of FIGS. 28–31 may be used in a procedure wherein a guidewire 320 is first inserted into a tubular vascular component TVC of a patient. Subsequently to the placement of guidewire 320, tubular member 292 with cutting element 284 is inserted into vascular component TVC over guidewire 320, as shown in FIG. 32. Then guidewire 320 is withdrawn from the patient and replaced with wire 286, as indicated in FIG. 33. Wire 286 is a kind of guidewire. The insertion of wire 286 through aperture 306 is facilitated by a curved inner surface 322 of tubular member 292 at the distal end thereof (FIG. 28).

Figure 34:
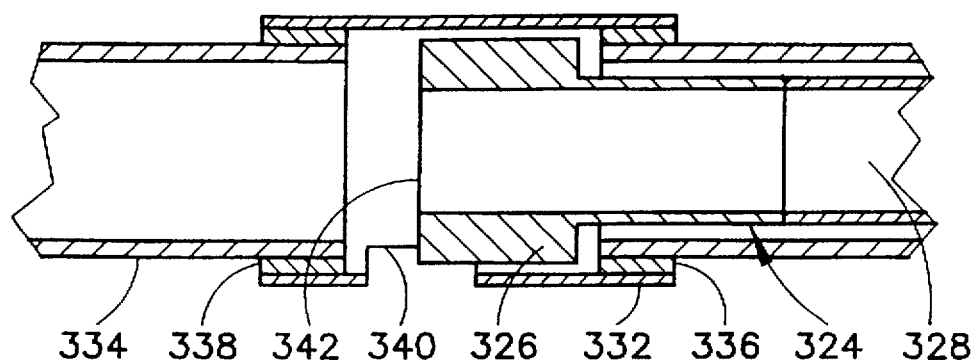
FIG. 34 is a schematic partial longitudinal cross-section view of a thrombectomy device in accordance with the present invention, illustrating a manufacturing technique.

FIG. 34 is provided to depict a manufacturing process for a partially flexible thrombectomy device as described herein. The process is, however, also applicable to completely rigid thrombectomy devices. A cutting element 324 including a rigid distal tip 326 and a flexible body 328 is inserted through a flexible outer tube 330. A rigid sleeve 332 is then attached to an outer surface of tube 330 and to another flexible tube 334 via annular welds or coupling elements 336 and 338. Sleeve 332 has a clot intake opening or port 340, while tip 326 of cutting element 324 is provided with a cutting edge 342.

Figure 35:
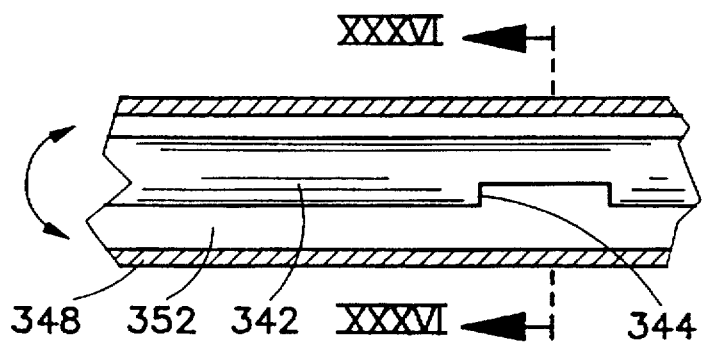
FIG. 35 is a schematic partial longitudinal cross-sectional view, on an enlarged scale, of yet another thrombectomy device in accordance with the present invention.
Figure 36:
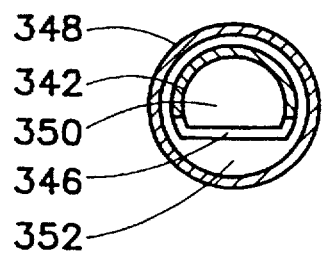
FIG. 36 is a transverse cross-sectional view taken along line XXXVI—XXXVI in FIG. 35.

FIGS. 35 and 36 depict a thrombectomy device with a cross-sectionally D-shaped cutter element 342 provided with a cutting window 344. A wall 346 of cutter element 342 divides a lumen (not designated) of a tubular member 348 into a suction channel 350 and an irrigation or positive pressurization channel 352. The cutter of FIGS. 35 and 36 may be reciprocated, or alternatively, rotated. In a rotating mode of operation, cutter element 342 remains longitudinally fixed relative to tubular member 348. As window 344 becomes aligned with an intake port (not shown) in tubular member 348, a negative pressure in suction channel 350 draws a clot or other organic material into the tubular member through the intake port. Further rotation of cutter element 342 closes the intake port and simultaneously cuts off a portion of the clot or other material for subsequent removal or ejection via the tubular member.

Figure 37:
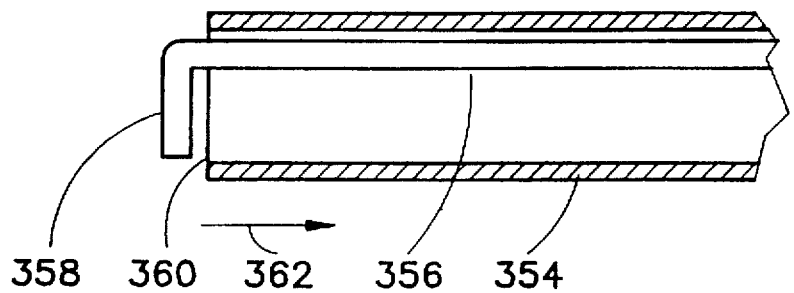
FIG. 37 is a schematic partial longitudinal cross-sectional view, on an enlarged scale, of yet a further thrombectomy device in accordance with the present invention.

As illustrated in FIG. 37, a thrombectomy device may include a tubular member 354 through which a hollow eccentrically disposed irrigation tube 356 slidably extends. At a distal end, irrigation tube or drive rod 356 is provided with a cap 358 which closes off a clot-intake port or opening 360 upon a shifting of the irrigation tube in the proximal direction, as indicated by an arrow 362. Upon the closure of intake port 360 by cap 358, fluid pressure from tube 356 may be built up in tubular member 354 to eject any stuck clot material.

Although the invention has been described in terms of particular embodiments and applications, one of ordinary skill in the art, in light of this teaching, can generate additional embodiments and modifications without departing from the spirit of or exceeding the scope of the claimed invention. For example, other configurations of the suction, irrigation and clot-intake ports and other clot cutting techniques will occur readily to those of ordinary skill in the art. These alternate configurations and cutting tools are considered to be equivalent to those disclosed specifically herein.

It is to be noted that a pressure sensor or other detector may be operatively connected to a suction line extending to the suction port of the clot removal device. Upon sensing a decrease in pressure, owing to the drawing of material into the clot intake port, the sensor automatically triggers a cutting and ejection phase of an operating cycle. Accordingly, the entire process may be automated (see discussion above with respect to FIG. 1 et seq.).

A device in accordance with the present invention may be used in internal organs other than blood vessels or vascular prostheses to remove material other than blood clots. Inside the vascular system, the device may be used to remove plaque and other vascular debris. The device may alternatively be used to remove tumorous growths and other undesirable tissues. In addition, the device may be used to remove organic material which has been macerated by another instrument or technique. In that event, the suction and tube pressurization procedures described herein, including the closing of the intake port to enable or enhance tube pressurization, can be used without the cutting operation, to remove the macerated material from a patient.

It is to be observed that an implanted prosthetic device such as a vascular bypass made of synthetic materials is considered to be an organ for purposes of the present invention. It is to be further observed that the cutting edges of cutter elements disclosed herein may be serrated or toothed, for facilitating the cutting operation.

It is also possible to provide a two-piece instrument with clot severing and ejection mechanisms in accordance with the present invention. In a two-piece instrument, two tubular parts are inserted into a patient at different locations so that the distal ends of the parts meet each other and can be connected inside the patient. Of course, one or more guidewires may be necessary, as well as locking elements at the distal ends of the two tubular parts for coupling the parts to form a single member.

Accordingly, it is to be understood that the drawings and descriptions herein are profferred by way of example to facilitate comprehension of the invention and should not be construed to limit the scope thereof.

What is claimed is:

1. A method for removing material from inside a patient, comprising:
    (a) providing an elongate tubular member having a suction part and an intake port, said suction port being spaced from said intake port;
    (b) inserting a portion of said tubular member through a skin surface of a patient and into an internal organ of the patient;
    (c) upon completion of said step of inserting, applying suction to said tubular member via said suction port to thereby draw material in said organ into said tubular member through said intake port;
    (d) upon a drawing of said material at least partially into said tubular member through said intake port, severing a portion of said material inside said tubular member;
    (e) upon severing of said material, closing said intake port to substantially seal said tubular member with respect to said organ;
    (f) upon closure of said intake port and the substantial sealing of said tubular member with respect to said organ, feeding fluid to said tubular member essentially upstream of the severed portion of said material to enable a forcible ejection of the severed portion of said material under positive pressure through said tubular member;
    (g) removing said tubular member from the patient; and
    (h) prior to removal of said tubular member, repeating steps (c) through (f) so that each severed portion of said material is ejected from said tubular member prior to removal thereof from the patient.

2. The method defined in claim 1 wherein said tubular member has an obturator part disposed inside a tubular part, an irrigation inlet port being disposed in said obturator part, the applying of fluid pressure to the severed portion of said material including the feeding of fluid along said obturator part and through said tubular part.

3. The method defined in claim 1 wherein the tubular member is provided with a movable or shiftable cutter element, the severing of said portion of said material including shifting said cutter element so that a cutting edge of said cutter element moves past said intake port, the closing of said intake port including blocking said intake port with said cutter element.

4. The method defined in claim 3 wherein the feeding of said fluid to said tubular member includes feeding said fluid through said tubular member and past said cutter element.

5. The method defined in claim 3 wherein said cutter element is provided with a fluid-flow channel, the feeding of said fluid including guiding said fluid through said channel.

6. The method defined in claim 3 wherein said tubular member is cylindrical, said cutter element having a D-shaped cross-section defining two parallel D-shaped channels, the feeding of fluid including the feeding of fluid into one of said channels.

7. The method defined in claim 1 wherein the feeding of fluid includes directing fluid along a path through said tubular member past said intake port.

8. The method defined in claim 7 wherein the tubular member is provided with a cutter element, said path extending past said cutter element, the severing of said portion of said material including shifting a cutting edge of said cutter element past said intake port.

9. The method defined in claim 8 wherein said cutter element is provided with a fluid-flow channel, said path extending through said channel.

10. The method defined in claim 7, further comprising closing said intake port during the feeding of fluid to said tubular member, thereby enabling an increase in pressure in said tubular member to forcibly eject the severed portion of said material from said tubular member.

11. The method defined in claim 1 wherein the feeding of fluid includes connecting a pressurizable fluid source to said tubular member and feeding fluid under pressure from said source and at least partially along said tubular member past said intake port.

12. The method defined in claim 1, further comprising the step of applying suction to said tubular member at a point downstream of said intake port to pull the severed portion of said material from said intake port along said tubular member.

13. The method defined in claim 1 wherein said organ is a vascular component and said suction port and an irrigation inlet port are located on opposite sides of said intake port, the inserting of said portion of said tubular member including inserting a selected end of said tubular member through said skin surface of the patient into said vascular component and subsequently out of said vascular component and said skin surface so that said suction port and said irrigation port are located outside the patient while said intake port is located in said vascular component.

14. The method defined in claim 13, further comprising:
    inserting a catheter with an inflatable balloon in a deflated configuration into said vascular component;
    subsequently inflating said balloon;
    after inflation of said balloon, pulling said catheter and said balloon along said vascular component towards an insertion point of said tubular member into said vascular component, whereby vascular debris is shifted along said vascular component toward said intake port.

15. The method defined in claim 1, further comprising longitudinally shifting said tubular member through said organ to remove material along an extended portion of said organ.

16. The method defined in claim 15 wherein at least a substantial part of said tubular member is made of a flexible material, the longitudinal shifting of said tubular member including bending said tubular member.

17. The method defined in claim 1 wherein said organ is a vascular component and said material comprises vascular debris, said tubular member being provided with a cutter element having an internally threaded bore, the severing of said portion of said vascular debris including shifting a cutting edge of said cutter element past said intake port, further comprising:
    inserting a first guidewire into said vascular component prior to insertion of said tubular member, the insertion of said tubular member including inserting said tubular member into said vascular component along said guidewire;

19 after insertion of said tubular member into said vascular component, removing said guidewire;

providing a second guidewire having an externally threaded segment;

after removal of said first guidewire from said tubular member, inserting said second guidewire into said tubular member;

upon insertion of said second guidewire into said tubular member, threading said segment to said bore to thereby attach said second guidewire to said cutter element; and after attachment of said second guidewire to said cutter element, moving said second guidewire to shift said cutter element past said intake port.

18. The method defined in claim 1 wherein said tubular member is provided on an inner surface with a constricting sleeve, said tubular element being further provided with a cutter element having a projection at a downstream end, the severing of said portion of said material including shifting a cutting edge of said cutter element past said intake port, further comprising the step of moving said projection into said sleeve after shifting of said cutting edge past said intake port, thereby reducing said severed portion of said material in size prior to pushing said severed portion of said material along said tubular member.

19. The method defined in claim 1 wherein the tubular member carries a movable cutter element provided with spring loading, the severing of said portion of said material including shifting said cutter element in a first direction so that a cutting edge of said cutter element moves past said intake port, further comprising shifting said cutter element in a second direction opposite said first direction after a severing of said portion of said material, the shifting of said cutter element in at least one of said first direction and said second direction being performed under action of said spring loading.

20. The method defined in claim 1 wherein the tubular member carries a movable cutter element, the severing of said portion of said material including shifting said cutter element in a first direction so that a cutting edge of said cutter element moves past said intake port, further comprising shifting said cutter element in a second direction opposite said first direction after a severing of said portion of said material, the shifting of said cutter element in at least one of said first direction and said second direction including the step of applying fluid pressure to said cutter element.

21. A device for removing material from inside a patient, comprising:

an elongate tubular member having a suction port and an intake port, said suction port being spaced from said intake port, said suction port being connectable to a vacuum generator for applying suction to said tubular member;

cutting means mounted to said tubular member for severing a portion of material drawn partially in through said intake port upon disposition of said tubular member through a skin surface so that said suction port is located outside the patient while said intake port is located in an internal organ of the patient;

fluid feed means operatively connected to said tubular member for feeding a fluid to said tubular member to cooperate with applied suction to move the severed material out of said tubular member through said suction port, said fluid feed means being disposed eccentrically relative to said tubular member at least in a region about said intake port; and closure means mounted to said tubular member for closing said intake port upon a severing of said portion of

20 said material by said cutting means and prior to ejection of the severed portion of said material by the applied suction and said fluid feed means.

22. The device defined in claim 21 wherein said cutting means includes a cutting edge of a movable element slidably mounted to said tubular member, said closure means including a surface of said movable element.

23. The device defined in claim 22 wherein said fluid feed means includes means for feeding said fluid past said movable element.

24. The device defined in claim 23 wherein said movable element is provided with a fluid-flow channel so that fluid fed by said fluid feed means flows through said channel.

25. The device defined in claim 23 wherein said tubular member is cylindrical, said movable element having a D-shaped cross-section defining two parallel D-shaped channels, said fluid feed means including one of said channels.

26. The device defined in claim 21 wherein said fluid feed means includes means for directing pressurized fluid along a path through said tubular member past said intake port.

27. The device defined in claim 26 wherein said tubular member is provided with a movable cutter element, said path extending past said cutter element.

28. The device defined in claim 21 wherein an irrigation inlet port is provided on a side of said intake port opposite said suction port.

29. The device defined in claim 21, further comprising a balloon mounted to an external surface of said tubular member and means connected to said balloon for alternately inflating and deflating said balloon.

30. The device defined in claim 21 wherein said cutting means includes a cutter element having an internally threaded bore, further comprising a guidewire having an externally threaded segment, said guidewire being connected to said cutter element via said internally threaded bore and said externally threaded segment.

31. The device defined in claim 21 wherein said tubular member is provided on an inner surface with a constricting sleeve, said tubular element being further provided with a cutter element having a projection at a downstream end, said projection being insertable into said sleeve after a shifting of said cutter element past said intake port, to thereby push the severed portion of said material through said sleeve and reduce said severed portion of said material in size prior to an ejection of said severed portion of said material by said fluid pressurizing means.

32. The device defined in claim 21 said cutting means includes a cutter element provided with spring loading.

33. The device defined in claim 21 wherein said cutting means includes a movable cutter element and fluid shifting means for applying fluid pressure to said cutter element to shift said cutter element in at least one direction along said tubular member during an operating cycle of the device.

34. The device defined in claim 21 wherein said tubular member has an obturator part disposed inside a tubular part, an irrigation inlet port being disposed in said obturator part.

35. The device defined in claim 34 wherein said cutting means includes a cutter element disposed at a distal end of said obturator part.

36. A device for removing material from inside a patient, comprising:

an elongate tubular member having a suction port and an intake port, said suction port being spaced from said intake port, said suction port being connectable to a vacuum generator for applying suction to said tubular member;

a cutter element movably disposed inside said tubular member for severing material sucked into said tubular member through said intake port and for closing said intake port upon a drawing of said material into said tubular member through said intake port;

fluid feed means operatively connected to said tubular member for feeding a fluid to said tubular member to cooperate with applied suction to move the severed material out of said tubular member through said suction port; and a drive rod extending through said tubular member to said cutter element, said drive rod being connected to said cutter element for moving said cutter element to sever debris at said intake port, said drive rod being eccentrically located relative to said tubular member at least in a region about said intake port.

37. The device defined in claim 36 wherein said fluid feed means includes means for feeding said fluid past said cutter element.

38. The device defined in claim 37 wherein said cutter element is provided with a fluid-flow channel so that fluid fed by said fluid feed means flows through said channel.

39. The device defined in claim 36 wherein an irrigation inlet port is provided on a side of said intake port opposite said suction port.

40. A device for removing material from inside a patient, comprising:

an elongate tubular member having a debris intake port and defining a waste removal channel extending from said intake port to a suction port at one end of said channel;

a cutter element movably disposed inside said tubular member for severing debris sucked into said tubular member through said intake port and for closing said intake port upon a drawing of said debris into said tubular member through said intake port; and irrigation means disposed at least partially inside said tubular member for feeding irrigation fluid to said tubular member essentially upstream of the severed debris to generate positive pressure behind the severed debris to move the severed debris through said waste removal channel to said suction port.

41. The device defined in claim 40 wherein said irrigation channel has an outlet port disposed upstream of debris severed by said cutter element.

42. The device defined in claim 41 wherein said outlet port is disposed in said cutter element.

43. The device defined in claim 40 wherein said irrigation means includes said drive rod, said irrigation channel being a lumen of said drive rod.

44. The device defined in claim 43 wherein said irrigation channel has an outlet port disposed in said drive rod.

45. The device defined in claims 40, further comprising a drive rod extending through said tubular member to said cutter element, said drive rod being connected to said cutter element for moving said cutter element to sever debris at said intake port, said drive rod being eccentrically located, relative to said tubular member, at least in a region about said intake port, said irrigation means being eccentrically disposed relative to said tubular member at least in a region about said intake port.

* * * * *